United States Patent [19]

Boucher et al.

[11] Patent Number: 5,596,088
[45] Date of Patent: Jan. 21, 1997

[54] DNA ENCODING THE HUMAN $P_{2U}$ RECEPTOR AND NULL CELLS EXPRESSING $P_{2U}$ RECEPTORS

[75] Inventors: Richard C. Boucher, Chapel Hill, N.C.; Gary A. Weisman, Columbia; John T. Turner, Ashland, both of Mo.; Thomas K. Harden; Claude E. Parr, both of Chapel Hill, N.C.; Daniel M. Sullivan; Laura J. Erb, both of Columbia, Mo.; Kevin D. Lustig, Cambridge, Mass.

[73] Assignees: The University of North Carolina At Chapel Hill, Chapel Hill, N.C.; The Curators of the University of Missouri, Columbia, Mo.

[21] Appl. No.: 442,134

[22] Filed: May 16, 1995

Related U.S. Application Data

[63] Continuation of Ser. No. 138,137, Oct. 15, 1993, abandoned.

[51] Int. Cl.⁶ .................................................. C12N 15/12
[52] U.S. Cl. ................... 536/23.5; 435/69.1; 435/240.2; 435/252.3; 435/254.11; 435/320.1
[58] Field of Search ............................ 435/240.2, 320.1, 435/252.3, 254.11, 69.1; 536/23.1, 23.5

[56] References Cited

U.S. PATENT DOCUMENTS 4,501,729  2/1985  Boucher et al. ........................ 424/45
5,240,846  8/1993  Collins et al. ......................... 435/240.1

FOREIGN PATENT DOCUMENTS

WO92/11016  7/1992  WIPO.
WO93/12756  7/1993  WIPO.

OTHER PUBLICATIONS

Brown et al., Mol. Pharmacology, 40, 648, 1991.
Murphy et al., J. Biol. Chem., 265, 11615, 1990.
Masu et al., Nature, 329, 836, 1987.
Wahl et al, Methods in Enzymology, 152, 415, 1987.
K. D. Lustic et al., *Expression cloning of an ATP receptor from mouse neuroblastoma cells*, Proc. Natl. Acad. Sci. 90, 5113–5117 (1993).
C. S. Stock, *Breathing Easier: A Promising Treatment for Cystic Fibrosis*, In: Endeavors: Research and Graduate Education at the University of North Carolina at Chapel Hill, 10, pp. 10–11 (Fall 1992).

*Primary Examiner*—Stephen G. Walsh
*Assistant Examiner*—Sally P. Teng
*Attorney, Agent, or Firm*—Bell, Seltzer, Park & Gibson

[57] ABSTRACT

Isolated DNAs encoding the human $P_{2U}$ receptor are disclosed, along with vectors and host cells containing the same and methods of using the same. Host cells which are essentially free of endogenous $P_{2U}$ receptor expression, and which express a heterologous $P_{2U}$ receptor such as a murine $P_{2U}$ receptor, are also disclosed, along with methods of using the same.

15 Claims, 2 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 1842 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 57..1181

( x i ) SEQUENCE DESCRIPTION: SEQ ID NO:1:

```
GGAACCCGTG CAGGCGCTGA GCATCCTGAC CTGGAGAGCA GGGGCTGGTC AGGGCG                    56

ATG GCA GCA GAC CTG GGC CCC TGG AAT GAC ACC ATC AAT GGC ACC TGG                 104
Met Ala Ala Asp Leu Gly Pro Trp Asn Asp Thr Ile Asn Gly Thr Trp
 1               5                  10                  15

GAT GGG GAT GAG CTG GGC TAC AGG TGC CGC TTC AAC GAG GAC TTC AAG                 152
Asp Gly Asp Glu Leu Gly Tyr Arg Cys Arg Phe Asn Glu Asp Phe Lys
                20                  25                  30

TAC GTG CTG CTG CCT GTG TCC TAC GGC GTG GTG TGC GTG CTT GGG CTG                 200
Tyr Val Leu Leu Pro Val Ser Tyr Gly Val Val Cys Val Leu Gly Leu
            35                  40                  45

TGT CTG AAC GCC GTG GGC CTC TAC ATC TTC TTG TGC CGC CTC AAG ACC                 248
Cys Leu Asn Ala Val Gly Leu Tyr Ile Phe Leu Cys Arg Leu Lys Thr
        50                  55                  60

TGG AAT GCG TCC ACC ACA TAT ATG TTC CAC CTG GCT GTG TCT GAT GCA                 296
Trp Asn Ala Ser Thr Thr Tyr Met Phe His Leu Ala Val Ser Asp Ala
65                  70                  75                  80

CTG TAT GCG GCC TCC CTG CCG CTG CTG GTC TAT TAC GCC CGC GGC                     344
Leu Tyr Ala Ala Ser Leu Pro Leu Leu Val Tyr Tyr Ala Arg Gly
                85                  90                  95

GAC CAC TGG CCC TTC AGC ACG GTG CTC TGC AAG CTG GTG CGC TTC CTC                 392
Asp His Trp Pro Phe Ser Thr Val Leu Cys Lys Leu Val Arg Phe Leu
                100                 105                 110

TTC TAC ACC AAC CTT TAC TGC AGC ATC CTC TTC CTC ACC TGC ATC AGC                 440
Phe Tyr Thr Asn Leu Tyr Cys Ser Ile Leu Phe Leu Thr Cys Ile Ser
            115                 120                 125
```

| | | | | | | | | | | | | | | | | |
|---|---|---|---|---|---|---|---|---|---|---|---|---|---|---|---|---|
|GTG|CAC|CGG|TGT|CTG|GGC|GTC|TTA|CGA|CCT|CTG|CGC|TCC|CTG|CGC|TGG|488|
|Val|His|Arg|Cys|Leu|Gly|Val|Leu|Arg|Pro|Leu|Arg|Ser|Leu|Arg|Trp| |
| |130| | | |135| | | |140| | | | | | | |

| | | | | | | | | | | | | | | | | |
|---|---|---|---|---|---|---|---|---|---|---|---|---|---|---|---|---|
|GGC|CGG|GCC|CGC|TAC|GCT|CGC|GGG|GTG|GCC|GGG|GCC|GTG|TGG|GTG|TTG|536|
|Gly|Arg|Ala|Arg|Tyr|Ala|Arg|Arg|Val|Ala|Gly|Ala|Val|Trp|Val|Leu| |
|145| | | |150| | | |155| | | | | | |160| |

| | | | | | | | | | | | | | | | | |
|---|---|---|---|---|---|---|---|---|---|---|---|---|---|---|---|---|
|GTG|CTG|GCC|TGC|CAG|GCC|CCC|GTG|CTC|TAC|TTT|GTC|ACC|ACC|AGC|GCG|584|
|Val|Leu|Ala|Cys|Gln|Ala|Pro|Val|Leu|Tyr|Phe|Val|Thr|Thr|Ser|Ala| |
| | | | |165| | | |170| | | | |175| | | |

| | | | | | | | | | | | | | | | | |
|---|---|---|---|---|---|---|---|---|---|---|---|---|---|---|---|---|
|CGC|GGG|CCG|CTA|ACC|TGC|CAC|GAC|ACC|TCG|GCA|CCC|GAG|CTC|TTC|AGC|632|
|Arg|Gly|Pro|Leu|Thr|Cys|His|Asp|Thr|Ser|Ala|Pro|Glu|Leu|Phe|Ser| |
| | | |180| | | |185| | | | |190| | | | |

| | | | | | | | | | | | | | | | | |
|---|---|---|---|---|---|---|---|---|---|---|---|---|---|---|---|---|
|CGC|TTC|GTG|GCC|TAC|AGC|TCA|GTC|ATG|CTG|GGC|CTG|CTC|TTC|GCG|GTG|680|
|Arg|Phe|Val|Ala|Tyr|Ser|Ser|Val|Met|Leu|Gly|Leu|Leu|Phe|Ala|Val| |
| | |195| | | |200| | | |205| | | | | | |

| | | | | | | | | | | | | | | | | |
|---|---|---|---|---|---|---|---|---|---|---|---|---|---|---|---|---|
|CCC|TTT|GCC|GTC|ATC|CTT|GTC|TGT|TAC|GTG|CTC|ATG|GCT|CGG|CGA|CTG|728|
|Pro|Phe|Ala|Val|Ile|Leu|Val|Cys|Tyr|Val|Leu|Met|Ala|Arg|Arg|Leu| |
| |210| | | |215| | | |220| | | | | | | |

| | | | | | | | | | | | | | | | | |
|---|---|---|---|---|---|---|---|---|---|---|---|---|---|---|---|---|
|CTA|AAG|CCA|GCC|TAC|GGG|ACC|TCG|GGC|GGC|CTG|CCT|AGG|GCC|AAG|CGC|776|
|Leu|Lys|Pro|Ala|Tyr|Gly|Thr|Ser|Gly|Gly|Leu|Pro|Arg|Ala|Lys|Arg| |
|225| | | |230| | | | |235| | | | | |240| |

| | | | | | | | | | | | | | | | | |
|---|---|---|---|---|---|---|---|---|---|---|---|---|---|---|---|---|
|AAG|TCC|GTG|CGC|ACC|ATC|GCC|GTG|GTG|CTG|GCT|GTC|TTC|GCC|CTC|TGC|824|
|Lys|Ser|Val|Arg|Thr|Ile|Ala|Val|Val|Leu|Ala|Val|Phe|Ala|Leu|Cys| |
| | | | |245| | | |250| | | | |255| | | |

| | | | | | | | | | | | | | | | | |
|---|---|---|---|---|---|---|---|---|---|---|---|---|---|---|---|---|
|TTC|CTG|CCA|TTC|CAC|GTC|ACC|CGC|ACC|CTC|TAC|TAC|TCC|TTC|CGC|TCG|872|
|Phe|Leu|Pro|Phe|His|Val|Thr|Arg|Thr|Leu|Tyr|Tyr|Ser|Phe|Arg|Ser| |
| | | |260| | | |265| | | | |270| | | | |

| | | | | | | | | | | | | | | | | |
|---|---|---|---|---|---|---|---|---|---|---|---|---|---|---|---|---|
|CTG|GAC|CTC|AGC|TGC|CAC|ACC|CTC|AAC|GCC|ATC|AAC|ATG|GCC|TAC|AAG|920|
|Leu|Asp|Leu|Ser|Cys|His|Thr|Leu|Asn|Ala|Ile|Asn|Met|Ala|Tyr|Lys| |
| | |275| | | |280| | | | |285| | | | | |

| | | | | | | | | | | | | | | | | |
|---|---|---|---|---|---|---|---|---|---|---|---|---|---|---|---|---|
|GTT|ACC|CGG|CTG|GCC|AGT|GCT|AAC|AGT|TGC|CTT|GAC|CCC|GTG|CTC|TAC|968|
|Val|Thr|Arg|Leu|Ala|Ser|Ala|Asn|Ser|Cys|Leu|Asp|Pro|Val|Leu|Tyr| |
|290| | | |295| | | | |300| | | | | | | |

| | | | | | | | | | | | | | | | | |
|---|---|---|---|---|---|---|---|---|---|---|---|---|---|---|---|---|
|TTC|CTG|GCT|GGG|CAG|AGG|CTC|GTA|CGC|TTT|GCC|CGA|GAT|GCC|AAG|CCA|1016|
|Phe|Leu|Ala|Gly|Gln|Arg|Leu|Val|Arg|Phe|Ala|Arg|Asp|Ala|Lys|Pro| |
|305| | | |310| | | |315| | | | |320| | | |

| | | | | | | | | | | | | | | | | |
|---|---|---|---|---|---|---|---|---|---|---|---|---|---|---|---|---|
|CCC|ACT|GGC|CCC|AGC|CCT|GCC|ACC|CCG|GCT|CGC|CGC|ACG|CTG|GGC|CTG|1064|
|Pro|Thr|Gly|Pro|Ser|Pro|Ala|Thr|Pro|Ala|Arg|Arg|Thr|Leu|Gly|Leu| |
| | | |325| | | |330| | | | |335| | | | |

| | | | | | | | | | | | | | | | | |
|---|---|---|---|---|---|---|---|---|---|---|---|---|---|---|---|---|
|CGC|AGA|TCC|GAC|AGA|ACT|GAC|ATG|CAG|AGG|ATA|GGA|GAT|GTG|TTG|GGC|1112|
|Arg|Arg|Ser|Asp|Arg|Thr|Asp|Met|Gln|Arg|Ile|Gly|Asp|Val|Leu|Gly| |
| | |340| | | |345| | | | |350| | | | | |

| | | | | | | | | | | | | | | | | |
|---|---|---|---|---|---|---|---|---|---|---|---|---|---|---|---|---|
|AGC|AGT|GAG|GAC|TCT|AGG|CGG|ACA|GAG|TCC|ACG|CCG|GCT|GGT|AGC|GAG|1160|
|Ser|Ser|Glu|Asp|Ser|Arg|Arg|Thr|Glu|Ser|Thr|Pro|Ala|Gly|Ser|Glu| |
| |355| | | |360| | | | |365| | | | | | |

| | | | | | | | |
|---|---|---|---|---|---|---|---|---|
|AAC|ACT|AAG|GAC|ATT|CGG|CTG|TAGGAGCAGA ACACTTCAGC CTGTGCAGGT|1211|
|Asn|Thr|Lys|Asp|Ile|Arg|Leu| | |
|370| | | | |375| | | |

| | | | | |
|---|---|---|---|---|---|
|TTATATTGGG|AAGCTGTAGA|GGACCAGGAC|TTGTGCAGAC|GCCACAGTCT|CCCCAGATAT|1271|
|GGACCATCAG|TGACTCATGC|TGGATGACCC|CATGCTCCGT|CATTTGACAG|GGGCTCAGGA|1331|
|TATTCACTCT|GTGGTCCAGA|GTCAACTGTT|CCCATAACCC|CTAGTCATCG|TTTGTGTGTA|1391|
|TAAGTTGGGG|GAATTAAGTT|TCAAGAAAGG|CAAGAGCTCA|AGGTCAATGA|CACCCCTGGC|1451|
|CTGACTCCCA|TGCAAGTAGC|TGGCTGTACT|GCCAAGGTAC|CTAGGTTGGA|GTCCAGCCTA|1511|
|ATCAAGTCAA|ATGGAGAAAC|AGGCCCAGAG|AGGAAGGTGG|CTTACCAAGA|TCACATACCA|1571|
|GAGTCTGGAG|CTGAGCTACC|TGGGGTGGGG|GCCAAGTCAC|AGGTTGGCCA|GAAAACCCTG|1631|
|GTAAGTAATG|AGGGCTGAGT|TTGCACAGTG|GTCTGGAATG|GACTGGGTGC|CACGGTGGAC|1691|

```
TTAGCTCTGA GGAGTACCCC CAGCCCAAGA GATGAACATC TGGGGACTAA TATCAATAGA    1751

CCCATCTGGA GGCTCCCATG GGCTAGGAGC CAGTGTGAGG CTGTAACTTA TACTAAAGGT    1811

TGTGTTGCCT GCTAAAAAAA AAAAAAAAA A                                    1842
```

( 2 ) INFORMATION FOR SEQ ID NO:2:

( i ) SEQUENCE CHARACTERISTICS:
            ( A ) LENGTH: 375 amino acids
            ( B ) TYPE: amino acid
            ( D ) TOPOLOGY: linear ( i i ) MOLECULE TYPE: protein ( x i ) SEQUENCE DESCRIPTION: SEQ ID NO:2:

```
Met Ala Ala Asp Leu Gly Pro Trp Asn Asp Thr Ile Asn Gly Thr Trp
 1               5                  10                  15

Asp Gly Asp Glu Leu Gly Tyr Arg Cys Arg Phe Asn Glu Asp Phe Lys
            20                  25                  30

Tyr Val Leu Leu Pro Val Ser Tyr Gly Val Val Cys Val Leu Gly Leu
        35                  40                  45

Cys Leu Asn Ala Val Gly Leu Tyr Ile Phe Leu Cys Arg Leu Lys Thr
    50                  55                  60

Trp Asn Ala Ser Thr Thr Tyr Met Phe His Leu Ala Val Ser Asp Ala
 65                  70                  75                  80

Leu Tyr Ala Ala Ser Leu Pro Leu Leu Val Tyr Tyr Ala Arg Gly
            85                  90                  95

Asp His Trp Pro Phe Ser Thr Val Leu Cys Lys Leu Val Arg Phe Leu
            100                 105                 110

Phe Tyr Thr Asn Leu Tyr Cys Ser Ile Leu Phe Leu Thr Cys Ile Ser
            115                 120                 125

Val His Arg Cys Leu Gly Val Leu Arg Pro Leu Arg Ser Leu Arg Trp
    130                 135                 140

Gly Arg Ala Arg Tyr Ala Arg Arg Val Ala Gly Ala Val Trp Val Leu
145                 150                 155                 160

Val Leu Ala Cys Gln Ala Pro Val Leu Tyr Phe Val Thr Thr Ser Ala
                165                 170                 175

Arg Gly Pro Leu Thr Cys His Asp Thr Ser Ala Pro Glu Leu Phe Ser
            180                 185                 190

Arg Phe Val Ala Tyr Ser Ser Val Met Leu Gly Leu Leu Phe Ala Val
            195                 200                 205

Pro Phe Ala Val Ile Leu Val Cys Tyr Val Leu Met Ala Arg Arg Leu
    210                 215                 220

Leu Lys Pro Ala Tyr Gly Thr Ser Gly Gly Leu Pro Arg Ala Lys Arg
225                 230                 235                 240

Lys Ser Val Arg Thr Ile Ala Val Val Leu Ala Val Phe Ala Leu Cys
                245                 250                 255

Phe Leu Pro Phe His Val Thr Arg Thr Leu Tyr Tyr Ser Phe Arg Ser
            260                 265                 270

Leu Asp Leu Ser Cys His Thr Leu Asn Ala Ile Asn Met Ala Tyr Lys
            275                 280                 285

Val Thr Arg Leu Ala Ser Ala Asn Ser Cys Leu Asp Pro Val Leu Tyr
    290                 295                 300

Phe Leu Ala Gly Gln Arg Leu Val Arg Phe Ala Arg Asp Ala Lys Pro
305                 310                 315                 320

Pro Thr Gly Pro Ser Pro Ala Thr Pro Ala Arg Arg Thr Leu Gly Leu
```

|     |     |     |     | 325 |     |     |     |     | 330 |     |     |     |     | 335 |     |
| --- | --- | --- | --- | --- | --- | --- | --- | --- | --- | --- | --- | --- | --- | --- | --- |
| Arg | Arg | Ser | Asp | Arg | Thr | Asp | Met | Gln | Arg | Ile | Gly | Asp | Val | Leu | Gly |
|     |     |     | 340 |     |     |     |     | 345 |     |     |     |     | 350 |     |     |
| Ser | Ser | Glu | Asp | Ser | Arg | Arg | Thr | Glu | Ser | Thr | Pro | Ala | Gly | Ser | Glu |
|     |     |     | 355 |     |     |     |     | 360 |     |     |     |     | 365 |     |     |
| Asn | Thr | Lys | Asp | Ile | Arg | Leu |
|     | 370 |     |     |     |     | 375 |

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CGCACCATTG CCTTGGTAC 19

( 2 ) INFORMATION FOR SEQ ID NO:4:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GAGGATATCC TAATGATGAT GATGATGATG TAGCCGAATG TCCTTAGTCT C 51

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

AATGGVACHT GGGARGGRGA YGAR 24

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GACGTGSAAR GGCAGMMAGC WGAGGGCGAA 30

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:7:

CTGGAATAGC ACCATCAATG G  21

(2) INFORMATION FOR SEQ ID NO:8:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:8:

GAGGTCAAGT GATCGGAAGG  20

DNA ENCODING THE HUMAN $P_{2U}$ RECEPTOR AND NULL CELLS EXPRESSING $P_{2U}$ RECEPTORS

This invention was made with Government support under Grant Nos. DHHS 5 R01 DE07389-08 and 5-P01-HL3422 awarded by the NIH. The Government has certain rights in the invention.

This is a continuation of application Ser. No. 08/138,137 filed on Oct. 15, 1993 now abandoned.

FIELD OF THE INVENTION

The present invention relates to DNA encoding $P_{2U}$ receptors, and particularly relates to DNA encoding the human $P_{2U}$ receptor, and null cells which express heterologous $P_{2U}$ receptors.

BACKGROUND OF THE INVENTION

Cystic fibrosis (CF) exhibits reduced Cl⁻ secretion by airway epithelia. Consequently, one of the most debilitating effects of CF is the development of a dehydrated, viscous mucus which obstructs the airways and compromises lung function. Extracellular nucleotide triphosphates, such as ATP or UTP, are able to regulate Cl⁻ secretion in human airway epithelia and, in combination with an inhibitor of $Na^+$ transport, may provide an alternative, non-CFTR-dependent mechanism to induce fluid secretion in CF airway epithelia. Extracellular nucleotides also stimulate mucus secretion by goblet cells in vitro and excessive activation of this pathway in vivo may be partly responsible for the hypersecretion observed in chronic bronchitis. In both cases, the responses are mediated by 5'-nucleotide ($P_{2U}$) receptors on the cell surface.

Recently, a cDNA encoding a murine ATP/UTP receptor was cloned from neuroblastoma cells by functional expression in Xenopus oocytes (K. Lustig et al., *Proc. Natl. Acad. Sci. USA* 90, 5113 (1993)). The receptor, a member of the G protein-coupled receptor superfamily, is activated by UTP and ATP, initiates elevation of cytoplasmic calcium, and has been identified with the subtype of $P_2$-receptor provisionally designated P2U. Its pharmacological and signaling properties are very similar to those described for a 5'-nucleotide ($P_{2U}$) receptor present in the human airway epithelial cell line, CF/T43, which was derived from a donor with CF (A. Brown et al., *Mol. Pharmacol.* 40, 648 (1991)).

Isolation and molecular characterization of the receptor for extracellular nucleotides present in human airway epithelia will permit studies of the expression of this receptor in normal and diseased tissues and facilitate identification of new drugs for therapy.

SUMMARY OF THE INVENTION

In view of the foregoing, a first aspect of the present invention is isolated DNA encoding an $P_{2U}$ receptor selected from the group consisting of: (a) isolated DNA (e.g., the DNA of SEQ ID NO:1) which encodes the human $P_{2U}$ receptor having the amino acid sequence given herein as SEQ ID NO:2; (b) isolated DNA which hybridizes to isolated DNA of (a) above and which encodes a human $P_{2U}$ receptor; and isolated DNA differing from the isolated DNAs of (a) and (b) above in nucleotide sequence due to the degeneracy of the genetic code, and which encodes a human $P_{2U}$ receptor.

A second aspect of the present invention is a recombinant DNA sequence comprising vector DNA and a DNA as given above which encodes an $P_{2U}$ receptor.

A third aspect of the present invention is a host cell containing a recombinant DNA sequence as given above and capable of expressing the encoded $P_{2U}$ receptor.

A fourth aspect of the present invention is isolated DNA as given above, and oligonucleotides as given above, configured in antisense for the production of antisense RNA which inhibits the expression of $P_{2U}$ receptor. (hereinafter referred to as "antisense DNAs"). Such antisense DNAs may be provided in a vector as given herein for transcription in a suitable cell where they then inhibit the production of the $P_{2U}$ receptor. In the alternative, antisense oligonucleotides which bind to RNA in cells and inhibit the expression of $P_{2U}$ receptor therein may be delivered directly to cells.

A fifth aspect of the present invention is a transformed null cell which is essentially free of endogenous $P_{2U}$ receptor expression, which null cell contains and expresses heterogenous DNA encoding an $P_{2U}$ receptor, said heterogenous DNA selected from the group consisting of: (a) isolated DNA consisting essentially of DNA which encodes the human $P_{2U}$ receptor having the amino acid sequence given herein as SEQ ID NO:2; (b) isolated DNA which hybridizes to isolated DNA of (a) above and which encodes a $P_{2U}$ receptor; and (c) isolated DNA differing from the isolated DNAs of (a) and (b) above in nucleotide sequence due to the degeneracy of the genetic code, and which encodes a $P_{2U}$ receptor.

A sixth aspect of the present invention is a method of detecting compounds which bind to the $P_{2U}$ receptor. The method comprises: (a) providing a cell which contains and expresses heterogenous DNA encoding a heterogenous $P_{2U}$ receptor, which cell secretes endogenous ATP in response to stimulation of said $P_{2U}$ receptor, the heterogenous DNA being as described above; (b) removing essentially all endogenous ATP secreted by said cell from said cell; (c) contacting a compound to said cell; and then (d) detecting the binding of the compound to the $P_{2U}$ receptor (e.g., by detecting an elevation in intracellular calcium therein).

A seventh aspect of the present invention is a method of enhancing cell growth, comprising transforming a cell with a vector capable of expressing a $P_{2U}$ receptor in the cell in an amount sufficient to enhance cell growth by autostimulation of the $P_{2U}$ receptor, where the cell secretes ATP which stimulates the $P_{2U}$ receptor, and where cell growth is enhanced by stimulation of the $P_{2U}$ receptor. The method is useful, among other things, for stimulating the growth of cultures of mammalian cells in vitro where the cells are difficult to grow or otherwise grow slowly in culture.

An eighth aspect of the present invention is a method of inhibiting cell growth, comprising transforming a cell with a vector capable of expressing a $P_{2U}$ receptor in the cell in an amount sufficient to inhibit cell growth by autostimulation of the $P_{2U}$ receptor, where the cell secretes ATP, and where cell growth is inhibited by stimulation of the $P_{2U}$ receptor. The method is useful, among other things, for inhibiting the growth of cells in vitro or in vivo such as in proliferative or hyperplastic diseases, both malignant and nonmalignant, of human and animal subjects.

A ninth aspect of the present invention is a method of treating diseases of epithelial mucosal surfaces (particularly diseases of airway epithelial mucosal surfaces such as cystic fibrosis, asthma, and chronic bronchitis) in a human or animal subject in need of such treatment by enhancing or inhibiting mucus production in that subject. The method is carried out by administering to the subject a vector capable of entering lung epithelial cells. The vector may be either:

(a) a vector which carries a DNA encoding a $P_{2U}$ receptor as described herein, which DNA is operably associated with a promoter which expresses that gene in the epithelial cells; or (b) a vector containing an antisense nucleic acid which encodes an antisense RNA, which antisense RNA is capable of binding to pre-mRNA encoding a $P_{2U}$ receptor and inhibiting expression thereof in the epithelial cells.

Also disclosed herein is a vector as described above, pharmaceutical formulations containing such a vector, and the use of such vectors for the preparation of a medicament the treatment of epithelial mucosal diseases in a subject in need of such treatment.

The foregoing and other aspects of the present invention are explained in detail below.

DETAILED DESCRIPTION OF THE INVENTION

Figure 1A:
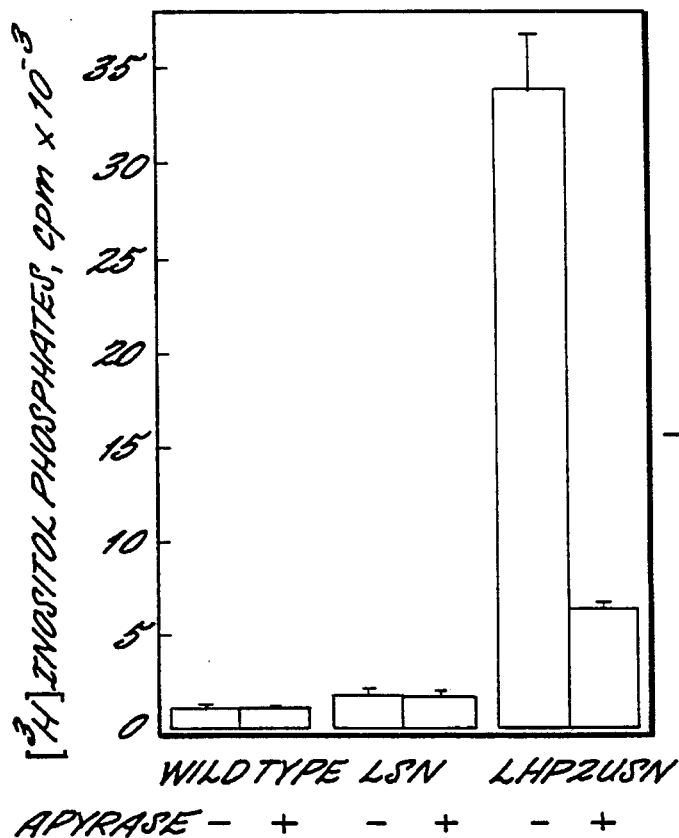
FIG. 1A shows [$^3$H] inositol phosphate production in cpm×10$^{-3}$ in wild type, LSN, and LHP2USN cells, with and without the present of apyrase in cells which had not been exposed to exogenous nucleotides.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., PatentIn User Manual, 99–102 (November 1990)(U.S. Patent and Trademark Office, Office of the Assistant Commissioner for Patents, Washington, D.C. 20231); U.S. Pat. No. 4,871,670 to Hudson et al. at Col. 3 lines 20–43 (applicants specifically intend that the disclosure of this and all other patent references cited herein be incorporated herein by reference).

Subjects treated by methods disclosed herein include both human subjects and animal subjects (e.g., dog, cat, horse) for veterinary purposes.

A. DNAs ENCODING $P_{2U}$ RECEPTORS AND OLIGONUCLEOTIDES THEREOF

DNAs which encode $P_{2U}$ receptors, whether they are cDNAs or genomic DNAs, encode a G-protein coupled receptor protein which, on expression in a suitable host cell, (a) selectively and stereospecifically binds ATP and UTP and (b) initiates the elevation of cytoplasmic calcium on binding ATP or UTP. This definition is intended to encompass natural allelic variations in the DNAs.

DNAs encoding $P_{2U}$ receptors which hybridize to the DNA encoding the human $P_{2U}$ receptor disclosed herein, may be of any species of origin, including murine (mouse, rat), rabbit, cat, porcine, and human, but preferably code for an $P_{2U}$ receptor of mammalian origin, and most preferably code for human $P_{2U}$ receptors.

Hybridization conditions which will permit other DNA sequences which code on expression for an $P_{2U}$ receptor to hybridize to a DNA sequence as given herein are, in general, high stringency conditions. For example, hybridization of such sequences may be carried out under conditions represented by a wash stringency of 0.3M NaCl, 0.03M sodium citrate, 0.1% SDS at 60° C. or even 70° C. to DNA disclosed herein in a standard in situ hybridization assay. (See J. Sambrook et al., Molecular Cloning, A Laboratory Manual (2d Ed. 1989)(Cold Spring Harbor Laboratory)). The same hybridization conditions are used to determine hybridization of oligonucleotides. In general, DNA sequences which code for $P_{2U}$ receptors and hybridize to the DNA sequence encoding the human $P_{2U}$ receptor disclosed herein will be at least 70%, 75%, 80%, 85%, 90%, or even 95% homologous or more with the sequence of the DNA encoding the human $P_{2U}$ receptor disclosed herein.

In general, DNA sequences which encode human $P_{2U}$ receptors which hybridize to the DNA encoding the human $P_{2U}$ receptor disclosed herein will be 93%, 94%, 95%, 96%, or even 97% homologous or more to the DNA sequence encoding the human $P_{2U}$ receptor disclosed herein.

Further, DNA sequences which code for the same $P_{2U}$ receptor as coded for by the foregoing sequences, but which differ in codon sequence from these due to the degeneracy of the genetic code, are also an aspect of this invention. The degeneracy of the genetic code, which allows different nucleic acid sequences to code for the same protein or peptide, is well known in the literature. See e.g., U.S. Pat. No. 4,757,006 to Toole et al. at Col. 2, Table 1.

B. GENETIC ENGINEERING TECHNIQUES

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

A vector is a replicable DNA construct. Vectors are used herein either to amplify DNA encoding $P_{2U}$ receptors as given herein and/or to express DNA which encodes $P_{2U}$ receptors as given herein. An expression vector is a replicable DNA construct in which a DNA sequence encoding a $P_{2U}$ receptor is operably linked to suitable control sequences capable of effecting the expression of the receptor in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Amplification vectors do not require expression control domains. All that is needed is the ability to replicate in a host, usually conferred by an origin of replication, and a selection gene to facilitate recognition of transformants.

Vectors comprise plasmids (e.g., the neomycin-resistance plasmid pP2R1 for stable transfection; the plasmids pCCM6×1 or pP2R for transient expression), viruses (e.g., adenovirus, cytomegalovirus), phage, and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

Transformed host cells are cells which have been transformed or transfected with vectors containing a DNA sequence as disclosed herein constructed using recombinant DNA techniques. Transformed host cells ordinarily express the receptor, but host cells transformed for purposes of cloning or amplifying the receptor DNA do not need to express the receptor.

Suitable host cells include prokaryote, yeast or higher eukaryotic cells such as mammalian cells and insect cells. Cells derived from multicellular organisms are a particularly suitable host for recombinant $P_{2U}$ receptor synthesis, and mammalian cells are particularly preferred. Propagation of such cells in cell culture has become a routine procedure (Tissue Culture, Academic Press, Kruse and Patterson, editors (1973)). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the DNA encoding the $P_{2U}$ receptor to be expressed and operatively associated therewith, along with a ribosome binding site, an RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter is often sufficient. Rather than using vectors which contain viral origins of replication, one can transform mammalian cells by the method of cotransformation with a selectable marker and the receptor DNA. Examples of suitable selectable markers are dihydrofolate reductase (DHFR) or thymidine kinase. This method is further described in U.S. Pat. No. 4,399,216.

Other methods suitable for adaptation to the synthesis of the $P_{2U}$ receptor in recombinant vertebrate cell culture include those described in M-J. Gething et al., *Nature* 293, 620 (1981); N. Mantei et al., *Nature* 281, 40; A. Levinson et al., EPO Application Nos. 117,060A and 117,058A.

Host cells such as insect cells (e.g., cultured *Spodoptera frugiperda* cells) and expression vectors such as the baculovirus expression vector (e.g., vectors derived from Autographa californica MNPV, Trichoplusia ni MNPV, Rachiplusia ou MNPV, or Galleria ou MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Prokaryote host cells include gram negative or gram positive organisms, for example *Escherichia coli* (*E. coli*) or Bacilli. Higher eukaryotic cells include established cell lines of mammalian origin as described below. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)). The promoter and Shine-Dalgarno sequence (for prokaryotic host expression) are operably linked to the DNA encoding the $P_{2U}$ receptor, i.e., they are positioned so as to promote transcription of $P_{2U}$ receptor messenger RNA from the DNA.

Eukaryotic microbes such as yeast cultures may also be transformed with vectors carrying the isolated DNA's disclosed herein. see, e.g., U.S. Pat. No. 4,745,057. Saccharomyces cerevisiae is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the receptor as given herein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)). Suitable vectors and promoters for use in yeast expression are further described in R. Hitzeman et al., EPO Publn. No. 73,657.

C. USES OF DNAS ENCODING $P_{2U}$ RECEPTORS.

$P_{2U}$ receptors made from cloned genes in accordance with the present invention may be used for screening compounds for $P_{2U}$ receptor activity, or for determining the amount of a $P_{2U}$ receptor agonist or antagonist such as ATP or UTP in a solution (e.g., blood plasma or serum), either for the purpose of quantitatively measuring the presence of the agonist or antagonist in the solution (e.g., in a standard laboratory assay), or screening for the presence or absence of that compound in the solution. For example, host cells may be transformed with a vector of the present invention, $P_{2U}$ receptors expressed in that host, the cells lysed, and the membranes from those cells used to screen compounds for $P_{2U}$ receptor binding activity. Competitive binding assays in which such procedures may be carried out are well known.

By selection of "null" host cells which do not ordinarily express $P_{2U}$ receptors (e.g., cells which are essentially free of endogenous $P_{2U}$ receptor expression, and more preferably cells which are essentially free of endogenous $P_{2X}$, $P_{2Y}$ and $P_{2U}$ receptor expression, which cells may or may not be essentially free of endogenous $P_{2T}$ receptor expression), preparations free of other $P_2$ receptors which might interfere with the assay can be obtained. Further, $P_{2U}$ receptor agonists and antagonists, particularly UTP and analogs thereof, can be identified by transforming host cells with vectors of the present invention, which host cells also express the several G-protein subunits and effector proteins necessary to cause the cell to initiate elevation of cytoplasmic calcium. $P_{2U}$ receptor agonists will initiate elevation of cytoplasmic calcium when they bind to and activate receptors expressed in such cells. Such cells must be capable of operatively associating the $P_{2U}$ receptor with the appropriate effector proteins: e.g., G protein must also be present in the cell membranes in the appropriate configuration. Such cells are typically mammalian cells, including human cells, examples being human leukemia cells (e.g., K562 human leukemia cells), and human astrocytoma cells (e.g., $1321N_1$ human astrocytoma cells).

As noted above, one particular method of detecting compounds which bind to the $P_{2U}$ receptor comprises (a) providing a cell which contains and expresses heterogenous DNA encoding a heterogenous $P_{2U}$ receptor, which cell secretes endogenous ATP which stimulates the $P_{2U}$ receptor, the heterogenous DNA being as described above; (b) removing essentially all endogenous ATP secreted by the cell from the cell (e.g., by inactivating the endogenous ATP or by separating the endogenous ATP from the cell); (c) contacting a compound to the cell; and then (d) detecting the binding of the compound to the $P_{2U}$ receptor. The method is particularly useful for detecting UTP and analogs thereof. The contacting step is typically carried out in an aqueous solution, though the cells can also be immobilized on a solid support for the assay. The removing step may be carried out by any suitable means, such as by including an enzyme in the solution which utilizes ATP as a substrate (e.g., including hexokinase and glucose in the aqueous solution in an amount sufficient so that essentially all of said ATP is utilized to phosphorylate the glucose; by including apyrase in the aqueous solution in an amount effective to degrade the ATP; etc.). Alternatively, the removing step may be carried out by washing the cell. The binding of the compound to the $P_{2U}$ receptor and activation of the receptor by agonists thereof may be detected by any suitable means, such as measuring for or detecting an elevation in intracellular calcium, measuring for or detecting an elevation in intracellular inositol phosphates, etc. Where only an indication of binding is desired, detection of binding may be carried out by any suitable means, such as with a competitive binding assay with a known agonist or antagonist.

Vectors which are capable of expressing a $P_{2U}$ receptor in a host cell are useful in methods of enhancing, facilitating, and/or accelerating cell growth. Such methods involve the step of transforming a cell with a vector capable of expressing a $P_{2U}$ receptor in the cell in an amount sufficient to enhance cell growth. Cell growth is enhanced by autostimulation of the $P_{2U}$ receptor, wherein the cell secretes ATP which activates the $P_{2U}$ receptor, and wherein cell growth is enhanced by activation of the $P_{2U}$ receptor (i.e., the binding of an agonist thereto). The vector may be as described above. The method is useful, among other things, for stimulating the growth of cultures of mammalian cells in vitro where the cells are difficult to grow or otherwise grow slowly in culture.

Vectors which are capable of expressing a $P_{2U}$ receptor in a host cell are also useful in methods of inhibiting or slowing cell growth. Such methods involve the step of transforming a cell with a vector capable of expressing a $P_{2U}$ receptor in the cell in an amount sufficient to inhibit or slow cell growth. Cell growth is inhibited by autostimulation of the $P_{2U}$ receptor, wherein the cell secretes ATP, and wherein cell growth is inhibited by activation of the $P_{2U}$ receptor. The vector may again be as described above. The method is useful, among other things, for slowing the growth cells in vitro where the cells are unduly proliferative, and for combatting proliferative or hyperplastic growth of cells or cell populations in a subject in need of such treatment, including both malignant and non-malignant cell growth (e.g., goblet cell hyperplasia).

Another aspect of the invention is antisense oligonucleotides (and DNAs encoding the same) having a sequence capable of binding specifically with any sequences of an mRNA molecule which encodes a human $P_{2U}$ receptor so as to prevent translation of the mRNA molecule (binding conditions may be at the stringencies as given above with respect to DNA hybridization). This method may be carried out in any patient where decreasing mucus secretion by downregulating epithelial cell (e.g., lung airway epithelial cell) cell $P_{2U}$ receptor expression is desired. This method may also be carried out in vitro or in a subject in need of such treatment for the purpose of slowing cell growth for the purposes described above. For example, in chronic bronchitis, the airway cell distribution is changed so that the number of goblet cells is increased and the number of ciliated cells is decreased. This phenomenon, known as goblet cell hyperplasia, is caused by chronic toxic exposure, and in patients afflicted with this disorder a means for decreasing mucus secretion by inhibiting $P_{2U}$ receptor expression in airway epithelial cells by administration of antisense nucleotides as described herein is desired. Other examples where such treatment may be desired include the treatment of gallblader epithelial mucos for cholecystitis and the treatment of liver biliary ducts for cholangitis. Where the antisense oligonucleotides are delivered directly to cells rather than via a DNA intermediate, nucleotides in which the phosphodiester bonds have been modified, e.g., to the methylphosphonate, the phosphotriester, the phosphorothioate, the phosphorodithioate, or the phosphoramidate, so as to render the oligonucleotide more stable in vivo may be used. Antisense oligonucleotides may be of any suitable length (e.g., from about 8 or 10 to 50 or 60 nucleotides in length), depending on the particular target being bound and the mode of delivery thereof. The antisense oligonucleotides are, in general, delivered or dosaged so that intracellular levels of the antisense oligonucleotide of from 0.05 to 50 µM are achieved.

Antisense oligonucleotides may be combined with an appropriate physiologically or pharmaceutically acceptable carrier (e.g., sterile pyrogen-free physiological saline solution) to provide a pharmaceutical formulation for delivery of the antisense oligonucleotide to cells, also in accordance with known techniques. See, e.g., U.S. Pat. No. 5,023,243 to Tullis). The antisense oligonucleotide in the formulation may be enclosed within a liposome, microcrystal, or other lipid vesicle to facilitate its being carried into the interior of cells, in accordance with known techniques, as also discussed above. Antisense oligonucleotides may also be delivered to cells by way of a DNA intermediate, as discussed in greater detail below.

In one embodiment, the present invention is carried out by administering to the subject a vector carrying a nucleic acid active agent, which vector is capable of entering epithelial mucosa cells (e.g., lung airway epithelial mucosa cells).

Such vectors may be formulated with pharmaceutical carriers and administered topically to the epithelial cells, such as by use of an aerosol delivery system in which respirable particles comprising the active agent to be delivered to the cells are generated and delivered to the airway surfaces of the subject. Suitable vectors are typically viral vectors, including DNA viruses (wherein the nucleic acid active agent is DNA) and RNA viruses, or retroviruses (wherein the nucleic acid active agent is RNA). Techniques for carrying out gene therapy are known and for the delivery of genetic materials to epithelial mucosa such as lung airway epithelial mucosa are known. See, e.g., F. Collins et al., U.S. Pat. No. 5,240,846; I. Pastan, U.S. Pat. No. 5,166,059; R. Debs et al., PCT Application WO 93/12756; T. Friedmann, *Science* 244, 1275 (1989).

DNAs of the present invention, and oligonucleotides derived therefrom, are useful for screening for restriction fragment length polymorphism (RFLP) associated with disorders such as cystic fibrosis or other disorders potentially involving a defective $P_{2U}$ receptor (or defective regulation thereof).

The present invention is explained in greater detail in the following Examples. These Examples are for illustrative purposes only, and are not to be taken as limiting of the invention.

EXAMPLE 1

Expression of Human $P_{2U}$ Receptor in Human Astrocytoma Cells

I. EXPERIMENTAL PROCEDURES

CDNA Cloning and Sequencing. Two degenerate oligonucleotide primers, 5'-AATGG(C/A/G)AC(C/T/A)TGG-GA(G/A)GG(G/A)GA(C/T)GA(A/G)-3' (SEQ ID NO:5), and 5'-GACGTG(C/G)AA(A/G)GGCAG(A/C)(A/C)AGC(A/T)GAGGGCGAA-3' (SEQ ID NO:6), from the N-terminal and transmembrane VI domains, respectively, of the murine P2U receptor sequence (Lustig et al., *Proc. Natl. Acad. Sci. USA* 90, 5113 (1993)), were used in a polymerase chain reaction to amplify products from a cDNA library constructed in lambda Uni-ZAP XR (Stratagene, La. Jolla, Cali.) from CF/T43 cell poly(A+) RNA. Amplification conditions were: 94° C., 1.5 min, 50° C., 1.5 min, 72° C., 2 min; 30 cycles. Products were cloned into pCR II (Invitrogen, San Diego, Calif., USA) and screened by Southern blot using a random primer-labeled fragment corresponding to bases 290–1097 (amino acid residues 8–276) of the murine $P_{2U}$ sequence (probe P263).

A cloned PCR product of about 500 bases (probe D9) which hybridized with probe P263 was labeled by random priming and used to screen 7×10⁵ recombinants of the CF/T43 cDNA library. Hybridization was performed using the QUIKHYB™ hybridization system (Stratagene) according to the manufacturer's instructions, except that 0.2×SSC/0.1% SDS was used for the high stringency wash. One plaque was identified which hybridized strongly with probe D9. After purification of phage by additional screening, pbluescript SK(−) was rescued by in vivo excision (Stratagene). An HT-29 cDNA library prepared in lambda gt10 was screened using probe P263, and insert from positive plaque-purified phage was subcloned into the Not I site of pbluescript. Plasmid DNA was purified by cesium chloride gradient centrifugation (Sambrook et al., Molecular Cloning: A Laboratory Manual (2d ed. 1989)) and both strands sequenced by dideoxy termination (Sequenase version 2.0; (United States Biochemical Corp., Cleveland, Ohio, USA).

Probe P263 was generated by high stringency PCR amplification of the murine P2U receptor clone, pP2R, obtained through the generosity of K. Lustig and D. Julius (Univ. of California, San Francisco, Calif., USA). The primers used to amplify P263 were: 5'-CTGGAATAGCACCATCAATGG-3' (SEQ ID NO:7) and 5'-GAGGTCAAGTGATCG-GAAGG-3' (SEQ ID NO:8).

Heterologous Expression. A retroviral vector-containing plasmid, pLHP2USN, was constructed by insertion of the cloned CF/T43 cDNA into the EcoRI and XhoI sites of pLXSN (A. Miller and G. Rosman, *Biotechniques* 7, 980 (1989)). An amphotrophic packaging cell line, PA317, was used to produce the LHP2USN retroviral vector and a control vector containing Neor only (LSN). Clonal human astrocytoma cells 1321N₁, UNC strain, generously provided by T. K. Harden (UNC, Chapel Hill, N.C.), were plated at 150,000 cells per 60-mm dish and infected with LHP2USN or LSN (2 hr, 4 ug/ml Polybrene) and after 48 hr selected with 600 ug/ml G418 (Life Technologies, Inc., Gaithersburg, Md., USA). To assay for receptor activity, intracellular calcium concentration was measured in confluent cells on coverslips by fura-2 fluorescence using microspectrofluorimetry as previously described (S. Mason et al., *Br. J. Pharmacol.* 103, 1649 (1991)). Measurement of cell inositol phosphate formation was as described by H. Brown et al., *Mol. Pharmacol.* 40, 648 (1991), in accordance with known techniques.

Northern and Southern Blots. Total cell and poly(A+) RNA were isolated by standard procedures or purchased commercially (Clontech, Palo Alto, Calif., USA). Human and mouse genomic DNA was extracted from cultured cells (Sambrook et al., supra) and digested (5 U/μg DNA) with KpnI, EcoRI, Bam HI, or XbaI. RNA (formaldehyde denatured) or restriction fragments of genomic DNA were resolved on agarose gels, transferred to Nytran or nitrocellulose membranes (Schleicher & Schuell) as described (Sambrook et al., supra), and UV-crosslinked (Stratagene). Prehybridization and hybridization of blots with cDNA probes were performed using the QUIKHYB™ hybridization system (Stratagene) as described above. Autoradiographs were done with Kodak XAR film and one intensifying screen at −80° C.

II. RESULTS AND DISCUSSION

A cDNA fragment from a human airway (CF/T43) cDNA library, amplified using degenerate primers based on the murine $P_{2U}$ receptor sequence, was used to obtain a full-length plasmid clone, pHAP2U, from the same library, which contains the insert sequence given herein as SEQ ID No:1. Concomitantly, low stringency screening with the murine $P_{2U}$ partial cDNA, P263, of an HT-29 cDNA library produced a clone which, upon sequence analysis, was found to contain cDNA identical to the pHAP₂ᵤ insert. The deduced amino acid sequence of an open reading frame (SEQ ID NO: 1 and SEQ ID NO:2) present in the human cDNA bears substantial similarity (89% identity) to the murine $P_{2U}$ receptor sequence reported by Lustig et al., supra, but is considerably less similar to the chick P2Y purinoceptor (37% identity) described by T. Webb et al., *FEBS Lett.* 324, 219 (1993).

The pHAP2U insert ($HP_{2U}$) sequence exhibits structural features typical of the family of G protein-coupled receptors and common to both the chick and murine P2-receptors. These include: (1) seven hydrophobic domains, (2) consensus N-linked glycosylation sequences near the N-terminus, (3) a number of residues highly conserved among G protein-coupled receptors (e.g., Asn51, Asp79, Cys106 and Cys183), and (4) potential phosphorylation sites in the third intracellular and C-terminal domains. The putative $P_{2U}$ receptor sequences also have a potential site for phosphorylation by protein kinase C in the second intracellular loop. Alignment of the human and murine $P_{2U}$ receptor sequences reveals 4 additional residues, as well as a number of mismatched residues, in the C-terminal intracellular domain of the human clone. Like the murine and chick $P_2$-receptors, the human $P_{2U}$ receptor sequence does not appear to be closely related to any of the other cloned G protein-coupled receptors, including those for adenosine and cAMP.

A retrovirus expression system was employed to study the cloned CF/T43 HP2U cDNA in 1321N1 human astrocytoma cells. The effect of extracellular nucleotides on intracellular calcium, as measured by fura-2 fluorescence, was assessed in CF/T43 cells, uninfected 1321N1 cells, and 1321N1 cells infected with retroviral vector containing either the cloned HP2U or no insert (LSN). Exposure of CF/T43 cells to extracellular UTP ($10^{-4}$M) resulted in an initial sharp increase in $[Ca^{2+}]_i$ which relaxed over 1–2 min to a prolonged plateau (data not shown). Application of UTP to CF/T43 cells in $Ca_{2+}$-free medium induced a sharp increase in $[Ca^{2+}]_i$ which returned to baseline without an intervening plateau phase. In contrast, extracellular UTP had no effect on uninfected 1321N1 cells (data not shown) or LSN-infected cells (data not shown), whereas carbachol elicited responses in each case. However, the $[Ca^{2+}]_i$ response of 1321N1 cells expressing the LHP2USN vector to UTP was similar to that of CF/T43 cells in both $Ca_{2+}$-free and $Ca_{2+}$-containing media (data not shown). In each experiment, the addition of ATP produced the same result observed with UTP. A response to extracellular nucleotides was seen in all trials with CF/T43 (peak $[Ca^{2+}]_i$=750+160 nM, n=10) and LHP2USN-expressing 1321N1 cells (peak $[Ca^{2+}]_i$=850+170 nM, n=6) but not with uninfected or LSN-infected controls.

To examine the pharmacological specificy of the HP2U clone expressed in 1321N1 cells, concentration-effect curves were generated for nucleotides and structural analogues active at $P_{2X}$, $P_{2Y}$ and $P_{2U}$ receptors (data not shown). UTP and ATP were equipotent, with $EC_{50}$ values of 1.4 and 1.0 uM, respectively, but UTP was slightly more efficacious. The $P_{2y}$ agonist, 2MeSATP, and $P_{2X}$ agonist, $\alpha,\beta$-MeATP, had little effect. These concentration-effect relations are very similar to those reported for heterologously expressed murine $P_{2U}$ (Lustig, et al., supra) and virtually indistinguishable from data (not shown) generated for the endogenous CF/T43 and HT-29 receptors. Clearly, the agonist specifities fit the defininition of the $P_{2U}$ receptor.

Pretreatment of CF/T43 and HP2U-1321N1 cells with pertussis toxin inhibited ATP-stimulated intracellular $Ca^{2+}$ mobilization in both cell-types by 20–30% (data not shown). These results are consistent with the effects of pertussis toxin on inositol phosphate accumulation induced by ATP or UTP in CF/T43 cells (Brown et al., supra (1991)), and on $P_{2U}$ responses in other systems (Murphy and Tiffany, J. Biol. Chem. 265, 11615 (1990)).

Figure 1B:
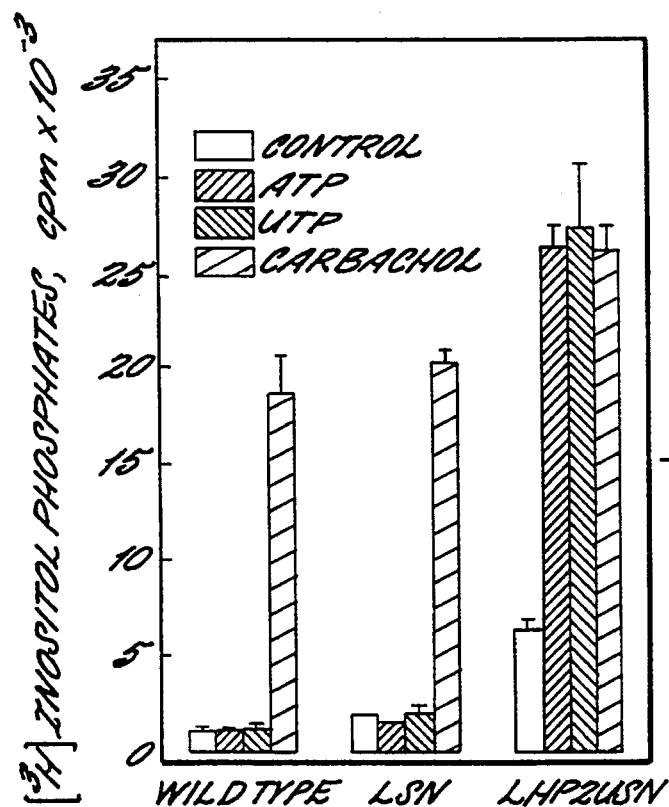
FIG. 1B shows [3H] inositol phosphate production in cpm×10$^{-3}$ in wild type, LSN, and LHP2USN cells, in cells which had been exposed to exogenous carbachol, UTP, and ATP, or cells which had not been exposed to exogenous compounds (control).

The pertussis toxin sensitivity of HP2U-1321N1 cells, along with the observation that UTP/ATP raised $[Ca^{2+}]_i$ in the absence of extracellular $Ca^{2+}$, suggest that $HP_{2U}$ is coupled to phospholipase C (PLC) via a G protein. To test this possibility more directly, we measured inositol phosphate formation. When these studies were first performed, very high levels of inositol phosphates were found to accumulate in $HP_{2U}$-1321N1 cells which had not been exposed to exogenous nucleotides (FIG. 1A). We hypothesized that during the lengthy labeling period 1321N1 cells released 5'-nucleotides into the medium in quantities sufficient to "self-activate" the receptor. The inclusion of apyrase in the medium during the cell-labeling step reduced the baseline inositol phosphate levels to values near those of controls (FIG. 1B). Thus, it appears the cells are persistently stimulated by nucleotides in an autocrine fashion. The mode of release of nucleotides from the astrocytoma cells and the biological consequences of the persistent autocrine activation are unknown. To facilitate comparison with controls, the inositol phosphate studies were performed on cells pretreated with apyrase. Consistent with coupling of the human $P_{2U}$ receptor to PLC, ATP and UTP increased inositol phosphate accumulation in 1321N1 cells expressing $LHP_{2U}SN$ but not in uninfected or LSN-infected controls (data not shown).

$P_{2U}$ receptor mRNA is widely distributed in human tissue: transcripts were detected in heart, liver, lung, and kidney, as reported for the mouse (Lustig et al., supra 1993), as well as placenta and skeletal muscle (data not shown). In addition, it was present in primary cultures of human respiratory epithelia and kidney proximal tubules, and in HSG-Pa salivary gland duct, CFT1 airway, and T84 colon cell lines.

Several of the human tissues and cell lines were found to express more than one mRNA. Transcripts of 2.1 kb, 7.5 kb, and 9 kb were observed, and in some tissues all three RNAs were present. -Although all of the bands in human tissues were found to cross hybridize with a full length murine $P_{2U}$ receptor cDNA, none of the murine tissues analyzed by Lustig et al., supra, or mouse skeletal muscle contain more than one transcript. Human liver and other human cells, including primary cultures of proximal tubule epithelium, were found to express only the 2.1 kb message, but both CF/T43 and HT-29 cells express at least two transcripts.

Although Murphy and Tiffany, supra, have reported that HL60 cells may express more than one mRNA coding for functional $P_{2U}$ receptors, the significance of multiple transcripts is unknown. If all of the bands represent fully processed mRNAs they may be alternatively processed forms of the same gene or products of different genes. Alternative processing might produce transcripts that differ in their noncoding regions but code for identical proteins. On the other hand, since the structure of $P_2$-receptor genes is unknown, the possibility remains that the different RNAs code for functionally different proteins, especially in light of the evidence presented below which suggests that at least two genes for $P_{2U}$ receptors exist in the human genome.

Human genomic DNA was digested with restriction enzymes known not to cut in the cDNA fragments used as probes. Under stringent conditions, a human $P_{2U}$ receptor coding sequence probe, D9, recognized two discrete bands in human genomic DNA cut with Kpn I, Eco RI, and Xba I, and three bands in DNA cut with Bam HI. The blot was then stripped and reprobed with a Kpn I fragment containing a segment of the 3' most bases of the $HP_{2U}$ clone. If the bands are portions of the same gene, only one would be associated with the 3' portion of the gene. In contrast, the $HP_{2U}$ Kpn I fragment recognized two bands in all of the digests (data not shown) suggesting that these bands are separate genes and not portions of the same gene. The downward shift of the more intensely hybridizing band in the Kpn I digest is consistent with the presence of a Kpn I site between the sequences recognized by the two probes. The lack of a shift in the position of the less intensely hybridizing band of the Kpn I digest and the loss of one of three bands in the Bam HI digest suggest that the second gene has lost the Kpn I site and that a Bam HI site has arisen in the portion recognized by the coding sequence probe. Both findings support the hypothesis that the probes are hybridizing to two unique genes.

A fragment from the coding region of the murine $P_{2U}$ receptor cDNA, probe P263, recognized a single band in mouse genomic DNA digested with either Eco RI or Bam HI. Whether these results correlate with the observation that human tissues appear to express more than one species of $P_{2U}$ message, while only one $P_{2U}$ receptor mRNA was found in mouse tissues, remains to be resolved.

EXAMPLE 2

Expression of Murine $P_{2U}$ Receptor in Human Leukemia Cells

I. EXPERIMENTAL PROCEDURES

Materials. pRc/CMV was purchased from Invitrogen (San Diego, Calif.). K562 human leukemia cells (CCL-243) were obtained from American Type Culture Collection (Rockville, Md.). Geneticin (G418) was purchased from GIBCO (Grand Island, N.Y.). Electroporation cuvettes (0.4 cm electrode gap) and the GENE PULSER™ electroporation chamber were obtained from Biorad (Richmond, Calif.). NYTRAN™ nylon membranes were purchased from Schleicher and Schuell (Keene, N.J.). [$\alpha$-$^{32}$P]ATP and [$\alpha$-$^{32}$P]UTP were obtained from ICN Radiochemicals (Irvine, Calif.). AVICEL™ microcrystalline silica gel thin layer chromatography plates containing a fluorescent indicator for nucleotides were obtained from Analtech (Newark, Del.). N,N-dimethylformamide and 4-benzoylbenzoic acid were obtained from Aldrich (Milwaukee, Wis.). HIS-BIND™ resin was purchased from Novagen (Madison, Wis.). ATPγS was purchased from Boehringer Mannheim (Indianapolis, Ind.) and 2-methylthioATP was purchased from Research Biochemicals Inc. (Natick, Mass.). Other reagents were purchased from Sigma (St. Louis, Mo.). Concentrations of nucleotide stock solutions were verified spectrophotometrically.

Cell Culture. K562 cells were cultured in spinner flasks (58 rpm) in growth medium (pH 7.4) composed of RPMI-1640, 10% heat-inactivated fetal bovine serum, 2 mM glutamine, 100 units/ml penicillin, and 100 μg/ml streptomycin. The cell suspensions were maintained at 37° C. in a humidified atmosphere of 5% $CO_2$ and 95% air at a density of $1\times10^5$ to $1\times10^6$ cells/ml.

Stable and Transient Transfections. To generate stable transfectants expressing the $P_{2U}$ receptor, K562 cells were transfected by electroporation (F. Toneguzzo et al., Mol. Cell. Biol. 6, 703 (1986)) with the neomycin-resistance plasmid pP2R1. pP2R1 is pRc/CMV containing a ~2.4 kb HindIII-NotI fragment of the $P_{2U}$ receptor cDNA, missing the first 6 nucleotides of the 5' untranslated region of the full length cDNA. control cells were stably transfected with pRc/CMV. Cells were sedimented at 200×g for 5 min at room temperature, rinsed once with phosphate-buffered saline (10 mM $NaH_2PO_4$, pH 7.4, 120 mM NaCl, 5 mM KCl), and resuspended in phosphate-buffered saline at a final concentration of $4\times10^7$ cells/ml. The cells were chilled on ice for 10 min and then transferred in 0.5 ml aliquots to prechilled electroporation cuvettes. DNA (40 μg of pP2R1 linearized with PvuI) was added to the cell suspension, the cells were subjected to a single electrical pulse (1 kV, 25 μF) and the cuvettes were placed on ice. After 10 min, growth medium was added and the cells were incubated at 37° C. Fresh growth medium supplemented with 0.7 mg/ml G418 was added 48 h later, and the cells were incubated for 2 weeks to select for stable transfectants expressing neomycin resistance. Clonal cell lines were then isolated by transferring single cells to individual wells of a 96-well culture plate: each well contained 0.2 ml of conditioned growth medium filtered from K562 stock cultures, 0.2 ml of fresh growth medium, and 0.4 mg/ml G418. The clonal cell lines were cultured for three to four weeks in growth medium containing 0.4 mg/ml G418 and assayed for $P_{2U}$ receptor, the results shown are from one representative clonal cell line.

To generate transient transfectants, K562 cells were transfected as above with 40 μg unlinearized plasmid pCCM6×or pP2R (Lustig et al., supra 1993). Cells were incubated for 48 h at 37° C. in 100 mm culture dishes containing 12 ml of growth medium and assayed for $P_{2U}$ receptor activity.

Cytoplasmic Free Calcium Measurements. Cells were sedimented at 200×g for 5 min at room temperature and washed once with 10 ml of Hepes-buffered saline (20 mM Hepes, pH 7.4, 120 mM NaCl, 5 mM KCl, 1 mM $MgCl_2$, and 1 mM $CaCl_2$). Washed cells were suspended in Hepes-buffered saline at $5\times10^5$ cells/ml, and stored (for up to 4 h) at 37° C. The concentration of cytoplasmic free calcium, $[Ca^{2+}]_i$, was measured by dual-excitation spectrofluorometric analysis of cells loaded with fura-2, a fluorescent probe for calcium.

Northern analysis. Poly $(A)^+$ RNA was isolated from K562 cells with a FastTrack® mRNA isolation kit (Invitrogen) and electrophoresed in 0.8% agarose-6.5% formaldehyde gels. The mRNA was transferred by capillary flow to a nylon membrane, prehybridized for 15 min at 68° C. in Quick-Hyb® (Stratagene), and hybridized for 1 h at 68° C. with random-primer labeled DNA synthesized in vitro from the Hind III-Not I fragment of pP2R. The membrane was washed twice at room temperature in 2×SSC containing 0.1% SDS, once at 60° C. in 0.2×SSC containing 0.1% SDS, and exposed to Kodak XAR film with an intensifying screen for 24 hr at −70° C.

Synthesis of [$\alpha$-$^{32}$P]BzATP and [$\alpha$-$^{32}$P]BZUTP. The following procedure was carried out in dim rom light to avoid photoactivation of the benzophenone moiety. 18 mg of 4-benzoylbenzoic acid (BzBz) and 42 mg of 1,1'-carbonyl-diimidazole were dissolved in 100 μl of N,N-dimethylformamide and stirred in a tightly stoppered 5 ml polypropylene test tube for 15 min at room temperature. Then, 0.5 ml of 3.3 μM [$\alpha$-$^{32}$P]ATP (3000 Ci/mmol) was added slowly and the reaction mixture was stirred overnight (approx. 15 h) at room temperature in a loosely stoppered test tube. The reaction mixture was centrifuged at 2000×g for 5 min and the supernatant was added to a Sephadex LH-20 column (1.5×45 cm) and eluted with 100 mM ammonium formate (pH 7.4) at a flow rate of 0.7 ml/min. The eluent was collected in 3.0 ml fractions and the fractions containing radioactivity were detected with a Geiger counter. Fractions 30–48 comprising the second radioactive peak ([$\alpha$-$^{32}$P]BzATP) were pooled, lyophilized, reconstituted in 1 ml of $H_2O$ and stored at −70° C. The amount of radioactivity in the [$\alpha$-$^{32}$P]BzATP sample was determined by liquid scintillation spectrometry and the concentration of [$\alpha$-32P]BzATP and [$\alpha$-$^{32}$P]ATP were equal. A 10–15% BzATP yield was obtained relative to the starting concentration of ATP. The purity of the [$\alpha$-$^{32}$P]BzATP sample was assessed by thin layer chromatography (TLC) on silica gel plates containing a fluorescent indicator for nucleotides. A TLC plate was spotted with 1 μl of the [$\alpha$-$^{32}$P]BzATP sample and other lanes were spotted with 5 nanomoles of unlabeled ATP, BzATP (Sigma Chemical Co.) and BzBz. The plate was developed for 2 h at room temperature in a chromatography chamber containing 100 ml of 1-butanol:$H_2O$:glacial acetic acid (5:3:2, v/v/v) and the nonradioactive standards were visualized by exposing the plate to short wavelength ultraviolet light. The $R_f$ values for ATP, BzATP and BzBz were 0.17, 0.65 and 0.98, respectively. An autoradiograph of the TLC plate indicated that the [α-32P]BzATP sample was >95% free of [α-$^{32}$P]ATP contamination. Synthesis of [α-$^{32}$P]BzUTP was performed as for [α-$^{32}$P]BzATP except that 0.5 ml of 3.3 µM [α-$^{32}$P]UTP (3000 Ci/mmol) was substituted for [α-$^{32}$P]ATP in the reaction mixture. The $R_f$ values of UTP and BzUTP were 0.21 and 0.70, respectively.

Construction and Purification of the Histidine-tagged $P_{2U}$ Receptor (P2HIS). To produce P2HIS, 70 pmoles of the primers CGCACCATTGCCTTGGTAC (SEQ ID NO:3) (which contains a BstXI site) and GAGGATATCCTAAT-GATGATGATGATGATGTAGCCGAATGTC-CTTAGTCTC (SEQ ID NO:4) (which contains an EcoRV site, stop codon, and the hexahistidine coding sequence) were incubated with 50 ng of pP2R, 20 nmoles of each dNTP, 1×reaction buffer (20mM Tris-HCl , pH 8.2, 10mM KCl, 6 mM $(NH_4)_2SO_4$, 1.5mM $MgCl_2$, and 0.1% Triton x-100), and $H_2O$ to bring the reaction mixture to a 100 µl volume. The reaction mixture was placed in a thermo-cycler and heated to 95° C. for 5 min prior to the addition of 2.5 units of Pfu DNA polymerase (Stratagene), a thermostable enzyme that possesses both 5' to 3' polymerase and 3' to 5' proofreading exonuclease activities. The reaction mixture was overlayed with 50 µl of mineral oil and subjected to 30 PCR cycles (95° C. for 1.5 min, 55° C. for 1.5 min, and 72° C. for 2 min). The PCR product, a single 400 bp band, was subcloned into the unique BstXI-EcoRV restriction site of pP2R to generate pP2HIS. K562 cells with stable P2HIS expression were produced by subcloning the HindIII-NotI restriction fragment of pP2HIS encoding the histidine-tagged $P_{2U}$ receptor cDNA into pRC/CMV and transfecting K562 cells as described for pP2R1. The composition of pP2HIS was verified by DNA sequence analysis.

To isolate P2HIS, plasma membranes from $10^8$ K562 cells with stable P2HIS expression were purified according to procedure of Thom et al. *Biochem. J.* 168, 187 (1977). The $P_{2U}$ receptors were then photolabeled by incubating 1 mg of plasma membrane protein in 2 ml of Hepes-EDTA buffer (20 mM Hepes, pH 7.5, 1 mM EDTA, 0.1 mM phenylmethyl-sulfonylfluoride, and 0.1 mM benzamidine) containing 5 nM [α-$^{32}$P]BzATP or 5 nM [α-$^{32}$P]BzUTP for 5 min at 37° C. followed by irradiation with long wavelength UV light for 15 min at 4° C. The irradiated membranes were washed twice with Hepes-EDTA buffer, pelleted by centrifugation at 35,000×g for 10 min at 4° C., and solubilized in 1 ml of urea buffer (6M urea, 500 mM NaCl, 20 mM Tris-HCl, pH 7.9). The solubilized proteins were applied to a $Ni^{2+}$-charged Sepharose column (2.5 ml bed volume) and eluted with an imidazole gradient. Column eluents wre dialyzed against 10 mM Tris-HCl (pH 7.4), lyophilized, and resolubilized in 50 µl of SDS-sample buffer. The samples were electrophoresed on a 5–16% SDS-polyacrylamide gel for approximately 16 h at 5 milliamps. The gel was dried and exposed to autoradiographic film for 1 to 3 days in order to visualize the radiolabeled proteins.

II. RESULTS AND DISCUSSION

ATP or UTP produced a two-fold increase in $[Ca^{2+}]_i$ in K562 cells stably or transiently transfected with $P_{2U}$ receptor cDNA (data not shown). $[Ca^{2+}]_i$ was maximal within 5 s after nucleotide addition and then returned to the basal level within 1 min. Neither ATP nor UTP elevated $[Ca^{2+}]^i$ in untransfected K562 cells or in vector-transfected K562 cells. In transient transfectants, the largest $P_{2U}$ receptor-mediated increases in $[Ca^{2+}]^i$ were observed 48 h after the transfection procedure.

In stable transfectants, the ATP- and UTP-mediated increases in $[Ca^{2+}]^i$ were not affected by depletion of extracellular $Ca^{2+}$ by EGTA (data not shown), suggesting that $P_{2U}$ receptor activation causes the mobilization of intracellular calcium and not the influx of extracellular calcium. Consistent with this idea, ATP and UTP also transiently reduced intracellular levels of phosphatidylinositol 4,5-bisphosphate ($PIP_2$) in the stable transfectants by approximately 10%. Activation of endogenous $P_{2U}$ receptors in NG108-15 cells similarly leads to the phospholipase C-dependent hydrolysis of $PIP_2$, the generation of inositol 1,4, 5-triphosphate ($IP_3$), and the mobilization of calcium from intracellular stores (Lin et al., *J. Neurochem.* 60, 1115 (1993)). The relatively weak effect of ATP and UTP on PIPz hydrolysis and calcium mobilization in K562 cells transfected with $P_{2U}$ receptor cDNA as compared to NG108-15 cells may reflect the low levels of IP3 receptors in undifferentiated K562 cells.

Figure 2:
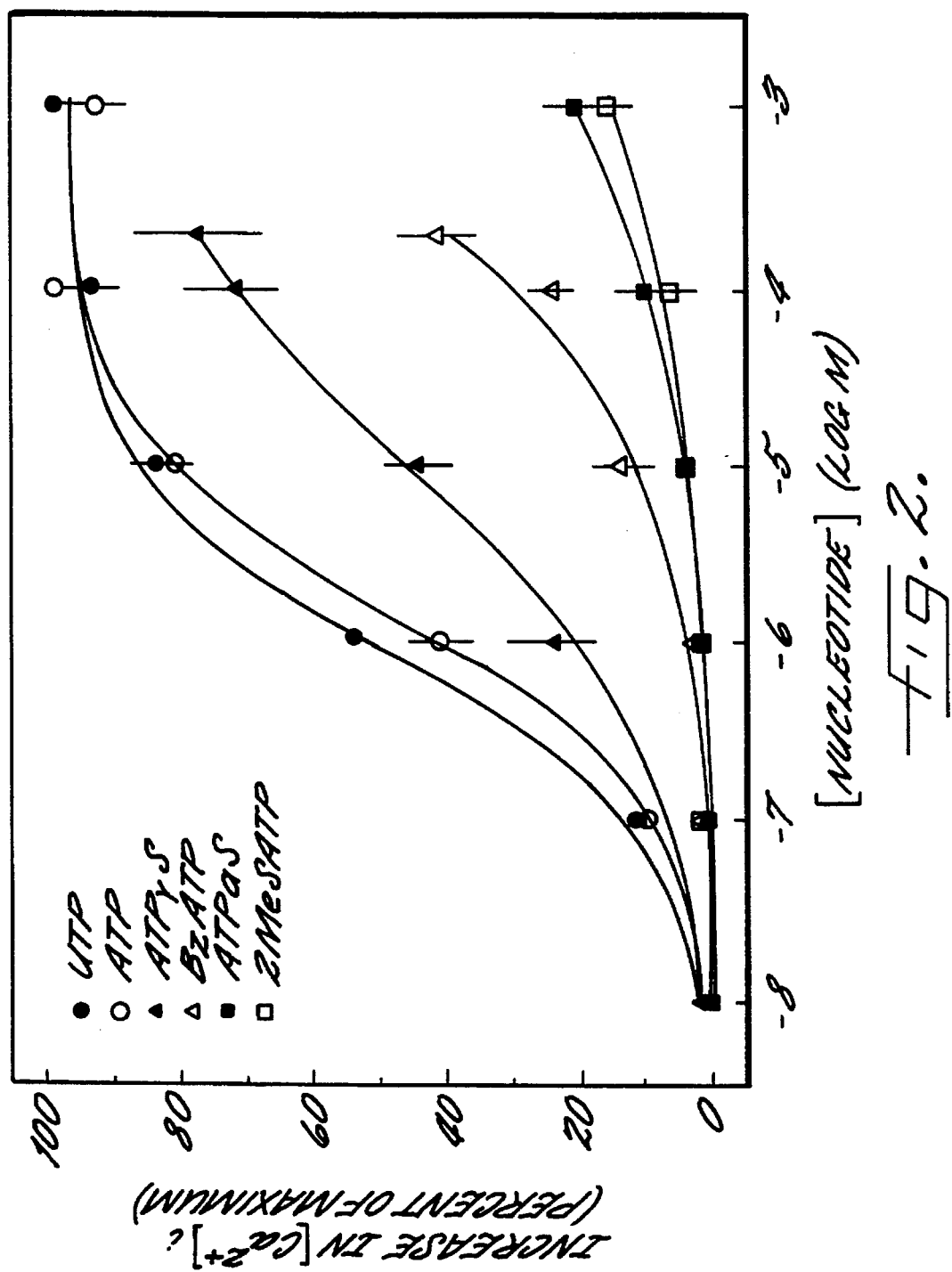
FIG. 2 shows the effect of nucleotides and nucleotide analogs on $[Ca^{2+}]_i$ in K-562 cells stably expressing a $P_{2U}$ receptor. $[Ca^{2+}]_i$ was measured after treatment with the indicated concentration of UTP (filled circles), ATP (open circles), ATPγS (filled triangles), BzATP (open triangles), ATPαS (filled squares), or 2-MeSATP (open squares).

It has been controversial whether ATP and UTP interact with the same receptor or whether the effect of each nucleotide is mediated by separate receptors. In stable transfectants, the $EC_{50}$ values for ATP- and UTP-mediated increases in $[Ca^{2+}]_i$ were about 1.4 µM and about 0.8 µM, respectively (FIG. 2). These responses are similar to those obtained in Xenopus oocytes expressing the $P_{2U}$ receptor where $EC_{50}$ values of about 1 µM were obtained for both nucleotides (Lustig et al., supra 1993). These findings demonstrate conclusively that the product of a single gene confers upon cells the ability to respond to both ATP and UTP.

K562 cells do not express an endogenous $P_{2U}$ receptor but do express a calcium-mobilizing $P_{2T}$ receptor that is activated by ADP and inhibited by ATP. In untransfected K562 cells, activation of the $P_{2T}$ receptor by ADP or 2-methylthioATP, but not 1 mM ATP, UTP, ATPγS, BzATP or BzUTP, elevated $[Ca^{2+}]_i$ (data not shown). ADP and 2-MeSATP do not appear to act as agonists of the $P_{2U}$ receptor, since the dose response curves for these nucleotides were virtually identical in stable transfectants and in vector-transfected K562 cells (FIG. 2). Similarly, ADP and 2-methylthioATP did not stimulate $^{45}Ca^{2+}$efflux in oocytes expressing the cloned receptor (Lustig et al., supra 1993). Hydrolysis of ATP may not be required for $P_{2U}$ receptor activation since the slowly-hydrolyzable ATP analog ATPγS was a relatively potent agonist ($EC_{50}$=about 9.6 µM) of the $P_{2U}$ receptor in stable transfectants (FIG. 2) and in Xenopus oocytes (Lustig et al., supra 1993). Furthermore, β,γ methyleneATP, β,γ imidoATP, GTP, TTP, CTP, UDP, AMP and adenosine, at concentrations as high as 1 mM, had no effect on $[Ca^{2+}]_i$; in untransfected K562 cells or stable transfectants, and did not prevent ATP-mediated increases in $[Ca^{2+}]_i$ in stable transfectants (not shown). Thus, these compounds do not appear to act as agonists or antagonists of the $P_{2U}$ receptor.

The photoaffinity probes 3'-O-(4-benzoyl)benzoyl adenosine 5'-triphosphate (BzATP) and 3'-O-(4-benzoyl)benzoyl uridine 5'-triphosphate (BzUTP) also were agonists of the $P_{2U}$ receptor (FIG. 2), although relatively weak agonists compared to ATP and UTP. BzATP has previously been used as an agonist and/or a photoaffinity probe for $P_{2Z}$ receptors in transformed mouse fibroblasts, and mouse macrophages, $P_{2Y}$ receptors in turkey erythrocytes, and $P_{2U}$ receptors in bovine endothelial cells and NG108-15 cells. This, however, is the first report of BzUTP as a $P_2$ receptor agonist.

Isolation of the $P_{2U}$ receptor and conclusive identification of its molecular weight were accomplished with the aid of a hexahistidine tag attached to the carboxy terminus of the $P_{2U}$ receptor protein (P2HIS). Both ATP and UTP caused an increase in $[Ca^{2+}]_i$ and a decrease in PIP2 (not shown) in K562 cells that stably express P2HIS, indicating that the agonist specificity and signaling properties of the $P_{2U}$ receptor were unaltered by the hexahistidine tag. P2HIS was isolated by affinity chromatography on $Ni^{2+}$-charged Sepharose columns. To increase detection of P2HIS, plasma membrane proteins from stable P2HIS transfectants were photolabeled with $[\alpha\text{-}^{32}P]BzATP$ or $[\alpha\text{-}32P]BzUTP$. The results indicated that a 53 kDa protein was selectively retained on the column until very high imidazole concentrations (200 mM) were used. The calculated molecular mass of the NG108-15 $P_{2U}$ receptor is 42 kDa, suggesting that the mature receptor is glycosylated on one or both of two N-linked glycosyation consensus sites located in its putative amino-terminal extracellular domain.

The $P_{2U}$ receptor cDNA encodes an mRNA of ~2.4 kb in a variety of tissues and cell lines (Lustig et al, supra 1993). Northern blot analysis revealed that a $P_{2U}$ receptor cDNA probe hybridized with an ~2.5 kb mRNA species in K562 cells that were transfected with P2R1 but did not hybridize with any transcript in untransfected K562 cells (data not shown). This suggests that the endogenous $P_{2T}$ receptor in K562 cells is not significantly homologous to the $P_{2U}$ receptor.

These results indicate that we have expressed a functional 53 kDa $P_{2U}$ receptor in K562 human leukemia cells. In stable and transient transfectants, the $P_{2U}$ receptor had the same agonist selectivity and signaling properties as in Xenopus oocytes and in NG108-15 cells, the source of the $P_{2U}$ receptor cDNA. Thus, our findings define a mammalian model system for rapidly analyzing structure-function relationships, radioligand-binding and signal transduction properties of both wild-type and mutant $P_{2U}$ receptors.

The foregoing examples are illustrative of the present invention, and are not to be construed as limiting thereof. The invention is defined by the following claims, with equivalents of the claims to be included therein.

That which is claimed is:

1. Isolated DNA encoding DNA human $P_{2U}$ receptor, selected from the group consisting of:
   (a) isolated DNA having SEQ ID NO:1; and (b) isolated DNA differing from the isolated DNA of (a) above in nucleotide sequence due to the degeneracy of the genetic code.

2. Isolated DNA which encodes DNA human $P_{2U}$ receptor having the amino acid sequence given herein as SEQ ID NO:2.

3. Isolated DNA having the sequence given herein as SEQ ID NO:1.

4. A vector comprising the DNA according to claim 1.

5. A vector according to claim 4, wherein said vector is selected from the group consisting of plasmids, adenoviruses, and cytomegaloviruses.

6. A vector according to claim 4, wherein said vector is a baculovirus vector.

7. A host cell containing a vector of claim 4 and capable of expressing the encoded $P_{2U}$ receptor.

8. A host cell according to claim 7, wherein said host cell is a mammalian cell.

9. A host cell according to claim 7, wherein said host cell is selected from the group consisting of baby hamster kidney cells, mouse cells, human embryo cells, and chinese hamster ovary cells.

10. A transformed null cell which is essentially free of endogenous $P_{2U}$ receptor expression, which null cell contains and expresses heterogenous DNA encoding a human $P_{2U}$ receptor, said heterogenous DNA selected from the group consisting of:
    (a) isolated DNA having SEQ ID NO:1; and
    (b) isolated DNA differing from the isolated DNA of (a) above in nucleotide sequence due to the degeneracy of the genetic code.

11. A cell according to claim 10, which cell is essentially free of endogeneous $P_{2X}$ and $P_{2Y}$ receptor expression.

12. A cell according to claim 10, which cell is a human leukemia cell.

13. A cell according to claim 10, which cell is a K562 human leukemia cell.

14. A cell according to claim 10, which cell is a human astrocytoma cell.

15. A cell according to claim 10, which cell is a $1321N_1$ human astrocytoma cell.

* * * * *

UNITED STATES PATENT AND TRADEMARK OFFICE
CERTIFICATE OF CORRECTION

PATENT NO. : 5,596,088
DATED : 21 January 1997
INVENTOR(S) : Boucher et al.

It is certified that error appears in the above-identified patent and that said Letters Patent is hereby corrected as shown below: On the title page: Item [56], foreign references, add class/subclass.

Col. 3, line 27, replace "[3H]" with --[$^3$H]--.

Col. 6, line 32, replace "see" with --See--.

Col. 10, line 52, replace "pHAP$_{2U}$" with --pHAP2U--.

Col. 10, line 62, replace "P2-receptors" with --P$_2$-receptors--.

Col. 11, line 31, replce "nuceotides" with --nucleotides--.

Col. 12, line 24, replace "-Although" with --Although--.

Col. 14, line 9, replace "pCCM6xor" with --pCCM6x1 or--.

Col. 14, line 16, replace "MgCI$_2$" with --MgCl$_2$--.

Col. 14, line 55, replace "[α-32P]" with --[α-$^{32}$P]--.

Col. 15, line 3, replace "[α-32P]" with --[α-$^{32}$P]--.

Col. 16, line 38, replace "$^{45}$Ca$^{2+}$efflux" with --$^{45}$Ca$^{2+}$ efflux--.

Col. 16, line 66, replace "PIP2" with --PIP$_2$--.

UNITED STATES PATENT AND TRADEMARK OFFICE
CERTIFICATE OF CORRECTION

PATENT NO. : 5,596,088

DATED : 21 January 1997

INVENTOR(S) : Boucher et al.

It is certified that error appears in the above-identified patent and that said Letters Patent is hereby corrected as shown below:

Col. 17, line 6, replace "$[\alpha\text{-}32P]$" with --$[\alpha\text{-}^{32}P]$--.

Col. 25, line 28, replace "DNA" with --a--.

Signed and Sealed this

Twenty-fourth Day of June, 1997

Attest:

BRUCE LEHMAN

Attesting Officer

Commissioner of Patents and Trademarks